(12) United States Patent
Stanus et al.

(10) Patent No.: US 7,942,861 B2
(45) Date of Patent: *May 17, 2011

(54) FLUID CONTAINER WITH ACCESS PORT AND SAFETY CAP

(75) Inventors: Johanny B. P. Stanus, Gibecq (BE); Eric J. Henaut, Arquennes (BE)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 507 days.

This patent is subject to a terminal disclaimer.

(21) Appl. No.: 12/051,507

(22) Filed: Mar. 19, 2008

(65) Prior Publication Data

US 2008/0208159 A1 Aug. 28, 2008

Related U.S. Application Data

(63) Continuation-in-part of application No. 11/139,244, filed on May 27, 2005, now Pat. No. 7,507,226, and a continuation-in-part of application No. 10/277,432, filed on Oct. 22, 2002, now Pat. No. 7,544,191.

(51) Int. Cl.
*A61M 1/36* (2006.01)

(52) U.S. Cl. .................... 604/414; 604/411; 604/415

(58) Field of Classification Search ............ 604/6.16, 604/264, 403, 408, 411, 414, 533, 200, 201, 604/204, 167.01, 167.03, 167.05, 27, 33, 604/905, 220; 383/210.1; 222/83, 96, 104, 222/153.05, 153.07, 548

See application file for complete search history.

(56) References Cited

U.S. PATENT DOCUMENTS

| 1,259,057 | A | 3/1918 | Vick |
| 2,073,292 | A | 3/1937 | Waite et al. |
| 2,849,256 | A | 8/1958 | Kowal |
| 3,512,524 | A | 5/1970 | Drewe |
| 3,653,546 | A | 4/1972 | Hazard |
| 3,844,283 | A | 10/1974 | Dabney |
| 3,986,508 | A | 10/1976 | Barrington |
| 4,062,466 | A | 12/1977 | Conti ........................ 215/252 |
| RE29,656 | E | 6/1978 | Chittenden et al. |
| 4,200,100 | A | 4/1980 | Willis |
| 4,201,208 | A | 5/1980 | Cambio, Jr. |

(Continued)

FOREIGN PATENT DOCUMENTS

CA 1333704 A1 12/1994

(Continued)

OTHER PUBLICATIONS

International Search Report for International Application No. PCT/US2006/019728 dated Oct. 26, 2006.

(Continued)

*Primary Examiner* — Leslie R Deak
(74) *Attorney, Agent, or Firm* — K&L Gates LLP

(57) ABSTRACT

An access port for a medical fluid container is provided and in one embodiment includes a shell and a perforator located within the shell, the perforator including an end configured to pierce a medical fluid container. The access port also includes a safety cap, the safety cap initially preventing the perforator from rotating relative to the plane of the container or piercing the container film. The safety cap is manually removable to enable the perforator to pierce the medical fluid container. The shell includes a pair of hinged moving arms and members hinged to the arms. The members push the perforator towards the medical fluid container when the arms are pushed downwardly.

20 Claims, 5 Drawing Sheets

U.S. PATENT DOCUMENTS

| | | | |
|---|---|---|---|
| 4,314,654 A | 2/1982 | Gaubert | |
| 4,322,018 A | 3/1982 | Rutter | |
| 4,364,387 A | 12/1982 | Larkin | |
| 4,405,163 A | 9/1983 | Voges et al. | |
| 4,416,395 A | 11/1983 | Gaubert | |
| 4,439,188 A | 3/1984 | Dennehey et al. | 604/534 |
| 4,475,566 A | 10/1984 | Haines | |
| 4,548,606 A | 10/1985 | Larkin | |
| 4,567,999 A | 2/1986 | Hjertman et al. | |
| 4,576,211 A | 3/1986 | Valentini et al. | |
| 4,632,673 A | 12/1986 | Tiitola et al. | |
| 4,676,775 A | 6/1987 | Zolnierczyk et al. | |
| 4,681,243 A | 7/1987 | Takasugi | |
| 4,696,411 A | 9/1987 | Graf et al. | |
| 4,735,608 A | 4/1988 | Sardam | |
| 4,767,407 A | 8/1988 | Foran | 604/164.06 |
| 4,785,858 A | 11/1988 | Valentini et al. | |
| 4,787,429 A | 11/1988 | Valentini et al. | |
| 4,798,605 A | 1/1989 | Steiner et al. | |
| 4,838,858 A | 6/1989 | Wortham et al. | |
| 4,872,494 A | 10/1989 | Coccia | |
| 4,909,290 A | 3/1990 | Coccia | |
| 4,927,423 A | 5/1990 | Malmborg | |
| 4,961,728 A | 10/1990 | Kosinski | |
| 4,973,310 A | 11/1990 | Kosinski | |
| 5,135,507 A | 8/1992 | Haber et al. | |
| 5,188,597 A | 2/1993 | Sweeney et al. | |
| 5,279,583 A | 1/1994 | Shober, Jr. et al. | |
| 5,297,696 A | 3/1994 | Bernstein et al. | |
| 5,304,192 A | 4/1994 | Crouse | |
| 5,308,347 A | 5/1994 | Sunago et al. | |
| 5,334,180 A * | 8/1994 | Adolf et al. | 604/411 |
| 5,337,775 A | 8/1994 | Lane et al. | |
| 5,352,191 A | 10/1994 | Sunago et al. | |
| 5,389,085 A | 2/1995 | D'Alessio et al. | |
| 5,425,367 A | 6/1995 | Shapiro et al. | |
| 5,445,630 A | 8/1995 | Richmond | |
| 5,456,678 A | 10/1995 | Nicoletti | |
| 5,480,385 A | 1/1996 | Thorne et al. | |
| 5,514,123 A | 5/1996 | Adolf et al. | |
| 5,542,927 A | 8/1996 | Shorne et al. | |
| 5,549,708 A | 8/1996 | Thorne et al. | |
| 5,603,706 A | 2/1997 | Wyatt et al. | |
| 5,616,129 A | 4/1997 | Mayer | |
| 5,616,130 A | 4/1997 | Mayer | |
| 5,685,863 A | 11/1997 | Botich et al. | |
| 5,709,667 A | 1/1998 | Carilli | |
| 5,746,727 A | 5/1998 | Graves et al. | |
| 5,766,147 A | 6/1998 | Sancoff et al. | |
| 5,769,138 A | 6/1998 | Sadowski et al. | |
| 5,795,336 A | 8/1998 | Romano et al. | |
| 5,810,398 A | 9/1998 | Matkovich | |
| 5,817,082 A | 10/1998 | Niedospial, Jr. et al. | |
| 5,868,433 A | 2/1999 | Matkovich | |
| 5,868,713 A | 2/1999 | Klippenstein | |
| 5,873,872 A | 2/1999 | Thibault et al. | |
| 5,895,383 A | 4/1999 | Niedospial, Jr. | |
| 5,960,992 A | 10/1999 | Bernstein et al. | |
| 5,975,163 A | 11/1999 | Gianfranco | |
| 5,976,115 A | 11/1999 | Parris et al. | |
| 6,050,978 A | 4/2000 | Orr et al. | |
| 6,068,617 A | 5/2000 | Richmond | 604/255 |
| 6,070,623 A | 6/2000 | Aneas | |
| 6,071,366 A | 6/2000 | Yamada | |
| 6,082,584 A | 7/2000 | Stern | |
| 6,131,767 A | 10/2000 | Savage et al. | 222/1 |
| 6,142,446 A | 11/2000 | Leinsing | |
| 6,161,728 A | 12/2000 | Dark | |
| 6,186,979 B1 | 2/2001 | Dysarz | |
| 6,220,482 B1 | 4/2001 | Simmel et al. | |
| 6,223,924 B1 | 5/2001 | Ek et al. | |
| 6,253,804 B1 * | 7/2001 | Safabash | 141/97 |
| 6,258,078 B1 | 7/2001 | Thilly | |
| 6,279,779 B1 | 8/2001 | Laciacera et al. | |
| 6,280,431 B1 | 8/2001 | Domkowski et al. | |
| 6,293,431 B1 | 9/2001 | Seymour et al. | |
| 6,341,802 B1 | 1/2002 | Matkovich | |
| 6,378,714 B1 | 4/2002 | Jansen et al. | |
| 6,478,771 B1 | 11/2002 | Lavi et al. | |
| 6,478,788 B1 | 11/2002 | Aneas | |
| 6,536,805 B2 | 3/2003 | Matkovich | |
| 6,537,263 B1 | 3/2003 | Aneas | |
| 6,540,732 B1 | 4/2003 | Botich et al. | |
| 6,601,721 B2 | 8/2003 | Jansen et al. | |
| 6,626,309 B1 | 9/2003 | Jansen et al. | |
| 6,645,181 B1 | 11/2003 | Lavi et al. | |
| 6,655,655 B1 | 12/2003 | Matkovich et al. | |
| 6,663,743 B1 | 12/2003 | Becker et al. | |
| 6,689,092 B2 | 2/2004 | Zierenberg et al. | |
| 6,709,424 B1 | 3/2004 | Knierbein | |
| 6,726,672 B1 | 4/2004 | Hanly et al. | |
| 6,786,875 B2 | 9/2004 | Barker et al. | |
| 7,507,226 B2 * | 3/2009 | Stanus et al. | 604/414 |
| 2001/0003996 A1 | 6/2001 | Jansen et al. | |
| 2002/0045843 A1 | 4/2002 | Barker et al. | |
| 2002/0058908 A1 | 5/2002 | Zierenberg et al. | |
| 2002/0093192 A1 | 7/2002 | Matkovich | |
| 2002/0121496 A1 | 9/2002 | Thiebault et al. | |
| 2002/0128628 A1 | 9/2002 | Fathallah | |
| 2002/0128629 A1 | 9/2002 | Antoine | |
| 2002/0193777 A1 | 12/2002 | Aneas | |
| 2004/0015126 A1 | 1/2004 | Zierenberg | |
| 2004/0015134 A1 | 1/2004 | Lavi et al. | |
| 2004/0078024 A1 | 4/2004 | Peluso et al. | |
| 2004/0078025 A1 | 4/2004 | Botich et al. | |
| 2005/0283132 A1 | 12/2005 | Stanus et al. | |

FOREIGN PATENT DOCUMENTS

| | | |
|---|---|---|
| EP | 0 280 528 A2 | 8/1988 |
| EP | 0 376 697 A2 | 7/1990 |
| EP | 0 376 698 A2 | 7/1990 |
| EP | 0 381 697 B1 | 8/1990 |
| EP | 0 416 545 A2 | 3/1991 |
| EP | 0416454 | 3/1991 |
| EP | 0 566 305 A3 | 10/1993 |
| EP | 0 568 525 B1 | 11/1993 |
| EP | 0 829 251 A3 | 3/1998 |
| EP | 0 954 249 B1 | 11/1999 |
| EP | 0 962 230 A3 | 12/1999 |
| EP | 0 988 871 B1 | 3/2000 |
| EP | 1 011 765 B1 | 6/2000 |
| EP | 1 029 526 | 8/2000 |
| EP | 1060730 | 12/2000 |
| EP | 1081054 | 3/2001 |
| EP | 1081054 | 7/2001 |
| LU | 90268 | 2/2000 |
| LU | 90268 | 4/2000 |
| LU | 90268 | 8/2007 |
| WO | WO 86/06966 | 12/1986 |
| WO | WO93/20772 | 10/1993 |
| WO | WO 93/20772 | 10/1993 |
| WO | WO 95/05863 | 3/1995 |
| WO | WO 97/36783 | 10/1997 |
| WO | WO 98/17192 | 4/1998 |
| WO | WO 98/44971 | 10/1998 |
| WO | WO 99/23947 | 5/1999 |
| WO | WO 00/24357 | 5/2000 |
| WO | WO 00/29049 | 5/2000 |
| WO | WO 00/35367 | 6/2000 |
| WO | WO 01/28490 | 4/2001 |
| WO | WO 01/60276 | 8/2001 |
| WO | WO 02/32372 | 4/2002 |
| WO | WO 03/100424 A3 | 12/2003 |
| WO | WO2004/037337 | 5/2004 |
| WO | WO 2004/060445 A2 | 7/2004 |

OTHER PUBLICATIONS

International Search Report (7 pgs).
European Search Report of EP 07015180.8 dated Sep. 20, 2007.
International Search Report from corresponding PCT application, PCT/US03/32398, mailed Jun. 2, 2004.
European Search Report Jan. 13, 2010 3 pages.

* cited by examiner

US 7,942,861 B2

FLUID CONTAINER WITH ACCESS PORT AND SAFETY CAP

CROSS REFERENCE TO RELATED APPLICATIONS

This application is a continuation-in-part of U.S. patent application Ser. No. 11/139,244, filed May 27, 2005, titled "Access Port with Safety Tab and Fluid Container Employing Same," which is a continuation-in-part of U.S. patent application Ser. No. 10/277,432, filed Oct. 22, 2002, titled "Formed, Filled, Sealed Solution Container, Port And Method For Establishing Flow Between The Container And An Administration Set." Each of these applications is hereby incorporated by reference in its entirety.

BACKGROUND

The present invention generally relates to a container, an access port and a method for establishing flow between the container and an administration set. The access port establishes flow of fluid from the container into an appropriate administration set. More specifically, a valve or base that seals to a container is provided. A perforator or plunger in the valve punctures the container and provides access to the solution in the container. A protective cap on the access port protects the access port and helps to maintain integrity and sterility of the connection.

Containers for the administration of medical solutions are well known. Typically, the containers are made from flexible film that is folded and sealed together along peripheral side edges. Further, the containers typically have an inlet and an outlet. The containers further typically have a device for piercing the outlet and establishing a fluid communication between the device and the solution inside the container. The solution may then be exhausted from the device to an administration set and/or patient.

Maintaining the sterility of the medical solution to be administered to the patient is extremely important. However, handling of the medical solution container may create risks of contamination. The risk of contamination may increase in emergency situations where quick manipulation of the various components may introduce bacteria or other pathogens into the container. For example, a user may inadvertently touch and/or contaminate a sterile end surface of an inlet or an outlet. The contamination may then be transferred to the contents of the container.

Further, containers for the administration of medical solutions are typically flexible. Accordingly, making an aseptic connection to the flexible container for withdrawing the contents in an aseptic manner may be difficult. For example, U.S. Reissue Pat. No. RE 29,656 to Chittenden et al. discloses an additive transfer unit having a tubular member that seals to a solution container. The unit includes a needle that punctures a stopper of the solution container. Obtaining a liquid-tight and leak-proof connection through the flexible container using traditional medical connectors such as, for example, needles or piercing pins is difficult.

Further, administration ports are securely bonded to the flexible container. However, the administration ports of known flexible solution containers are often the weakest part of the container. Accordingly, certain medical solutions, which are sensitive to oxygen and/or other penetrating gases, may be compromised. Further, preformed administration ports constitute potential sites of leakage and are potential points of contaminant ingress.

Other means for establishing a fluid connection between the container and an administration set are also known. Generally, known access ports require a two-handed operated access port and do not produce audible or visible notification when the access port is fully engaged. Further, many of the known access ports do not substantially protect against touch and airborne contaminants.

A need therefore exists for a formed, filled, sealed solution container with an access port and a method for establishing flow between the container and an administration set. Further, a medical solution container and access port with improved ease of access is needed. Further still, a solution container and a protected, covered access port with a liquid tight seal to avoid leaking, minimize touch and/or airborne contamination and minimize permeation of oxygen and other gases are needed. Additional features and advantages are described herein, and will be apparent from, the following Detailed Description and the figures.

SUMMARY

Embodiments of the present invention provide solutions to these problems. A first embodiment provides an access port. The access port includes a shell adapted for connection to a fluid container, a perforator located within the shell and capable of axial movement therein, the perforator including a first end configured to pierce a medical fluid container and a second end configured to connect to a fluid carrying device. The access port also includes a removable safety cap configured to fit over the second end, the cap adapted to impede axial movement of the perforator while coupled to the second end. In some embodiments, the safety cap further comprises a ring protrusion configured to fit inside the shell to impede rotation of the shell relative to the plane of the medical fluid container, and wherein a fit of the safety cap over the second end is a friction fit between the ring protrusion and the perforator or between the ring protrusion and the shell. The access port may also include an O-ring seal around the perforator to prevent leakage of fluid after the perforator pierces the medical fluid container.

Another embodiment provides an access port. The access port includes a perforator including a piercing end configured to pierce a medical fluid container and a connecting end adapted to connect to a fluid conduit, a shell positioned outside of the perforator, the shell including a body and a pair of arms connected hingedly to the body and extending angularly away from the body toward the piercing end of the perforator, the shell further including members each having a first end connected hingedly to one of the arms and a second end contacting the perforator, the members operable to push the perforator towards the medical fluid container when the arms are pushed towards the body of the shell. The access port also includes a cap, the cap configured to cover the connecting end of the perforator and to prevent the perforator from piercing the medical fluid container until the cap is removed. In some embodiments, the cap further comprises a ring protrusion fitting closely within the shell.

Another embodiment provides a medical fluid container assembly. The medical fluid container assembly includes at least one flexible film forming a fluid tight container, an access port with a shell configured to be coupled to the container, a perforator located within the shell and capable of axial movement therein, the perforator including a first end configured to pierce a medical fluid container and a second end configured to connect to a fluid carrying device, and a removable safety cap configured to cover one end of the access port, the cap adapted to impede axial movement of the perforator while coupled to the second end. In some embodiments, the safety cap further comprises a ring protrusion configured to fit inside the access port to impede rotation of the shell relative to the plane of the medical fluid container, and wherein a fit of the safety cap over the access port is a friction fit between the ring protrusion and the perforator or between the ring protrusion and the shell. There are many embodiments of the invention, only a few of which are described in the figures and detailed description below.

DETAILED DESCRIPTION

Embodiments may provide for a single-handed operation and may provide audible and visible notification when a perforator has punctured a film in a fluid bag to allow solution flow from a container. Further, the embodiments may inhibit contamination by fully shrouding the fluid generation path to exclude touch and air-borne contamination and not allowing for the removal of the perforator or plunger from the fluid engagement position, after engagement is achieved. Still further, the embodiments may reduce the amount of force needed to penetrate the film of the container.

Figure 1:
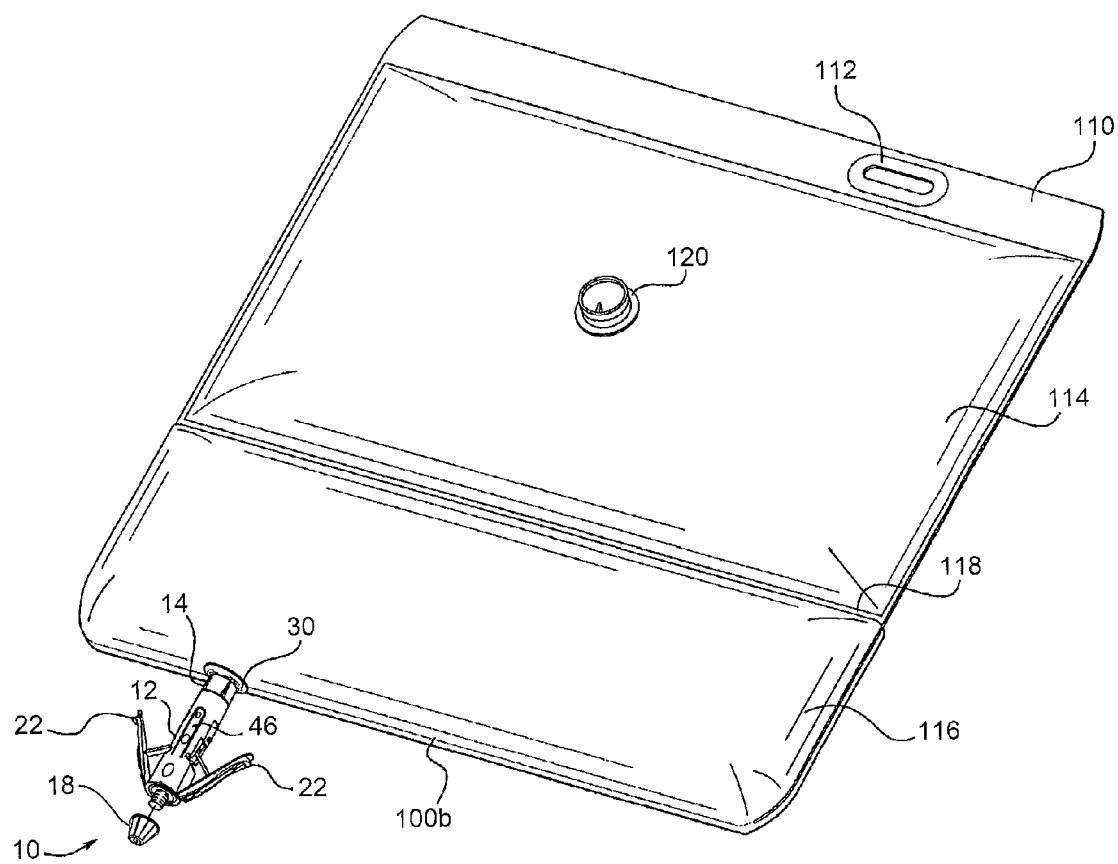
FIG. 1 is a perspective view of one embodiment of a medical fluid container, valve and access port.

Referring now to FIG. 1, one embodiment of an access port is illustrated via perforation assembly 10, which is connected to a solution container 100, such as a dialysate bag. Solution container 100 can be constructed by folding a film and sealing the film along the sides of the film. The folded film may then be filled with a medical solution and then sealed along the top to form a sealed, fluid-filled container. Container 100 may be constructed from a transparent material, for example, a multilayer ClearFlex™ material. In one embodiment, container 100 includes a medication port 120 that is adapted to receive a medication additive. As illustrated, medication port 120 in one implementation includes an injection site protected by a plastic cap.

Container 100 also includes a flap 110 with a reinforced hanger 112, which enables container 100 to be hung vertically if desired. Hanger 112 is placed at the top of container 100, so that perforation assembly 10 extends downwardly enabling solution to be gravity fed and/or to aid a pump in pumping the solution.

As illustrated, container 100 is a multi-compartment container including a first compartment 114 and a second compartment 116. Compartment 114 holds a first fluid, such as a dextrose-and-electrolyte component of a peritoneal dialysis or parenteral nutrition solution. Compartment 116 holds a second fluid, such as a bicarbonate buffer component of a peritoneal dialysis solution or an amino acid component of a parenteral nutrition solution. When seal 118 is ruptured or broken, the first and second fluids mix to form the completed medical solution, for example a dialysate that is delivered to the patient's peritoneal cavity or a parenteral nutrition solution that may be administered intravenously. One suitable multi-compartment bag is described in U.S. Pat. No. 6,663,743, assigned to the assignee of the present application, the entire contents of which are incorporated herein by reference.

Container 100 includes a valved output 30, through which a medical solution is delivered to the patient. In one embodiment valve 30 has a liner constructed from an elastomeric material, such as, for example, the same material used for compartments 114 and 116. Perforation assembly 10 connects, e.g., snap-fits, onto a port extending from valve 30. An administration line, such as a tube, is connected to the opposite end of perforation assembly 10, which in turn is connected to an object, such as a disposable cassette, patient, other bag, etc.

Perforation assembly 10 includes a shell 12. Shell 12 includes a bottom portion 14 that snap-fits over the port extending from valve 30 sealed to solution container 100. As seen best in FIGS. 2 to 5, bottom portion 14 of shell 12 includes a plurality of separate flanged sections 14a to 14d. The separate sections can flex to snap-fit over the port extending from valve 30 of container 100.

Shell 12 encloses a perforator 16. Shell 12 and perforator 16 are made of any suitable medically compatible material, such as any plastic that may be sterilized via gamma radiation, ethylene oxide or steam. Specifically, suitable materials include polypropylene (PP), polycarbonate (PC), polystyrene (PS), polyoxymethylene (POM), acrylonitrile-butadiene-styrene (ABS), and many other medically acceptable plastics.

Figure 4:
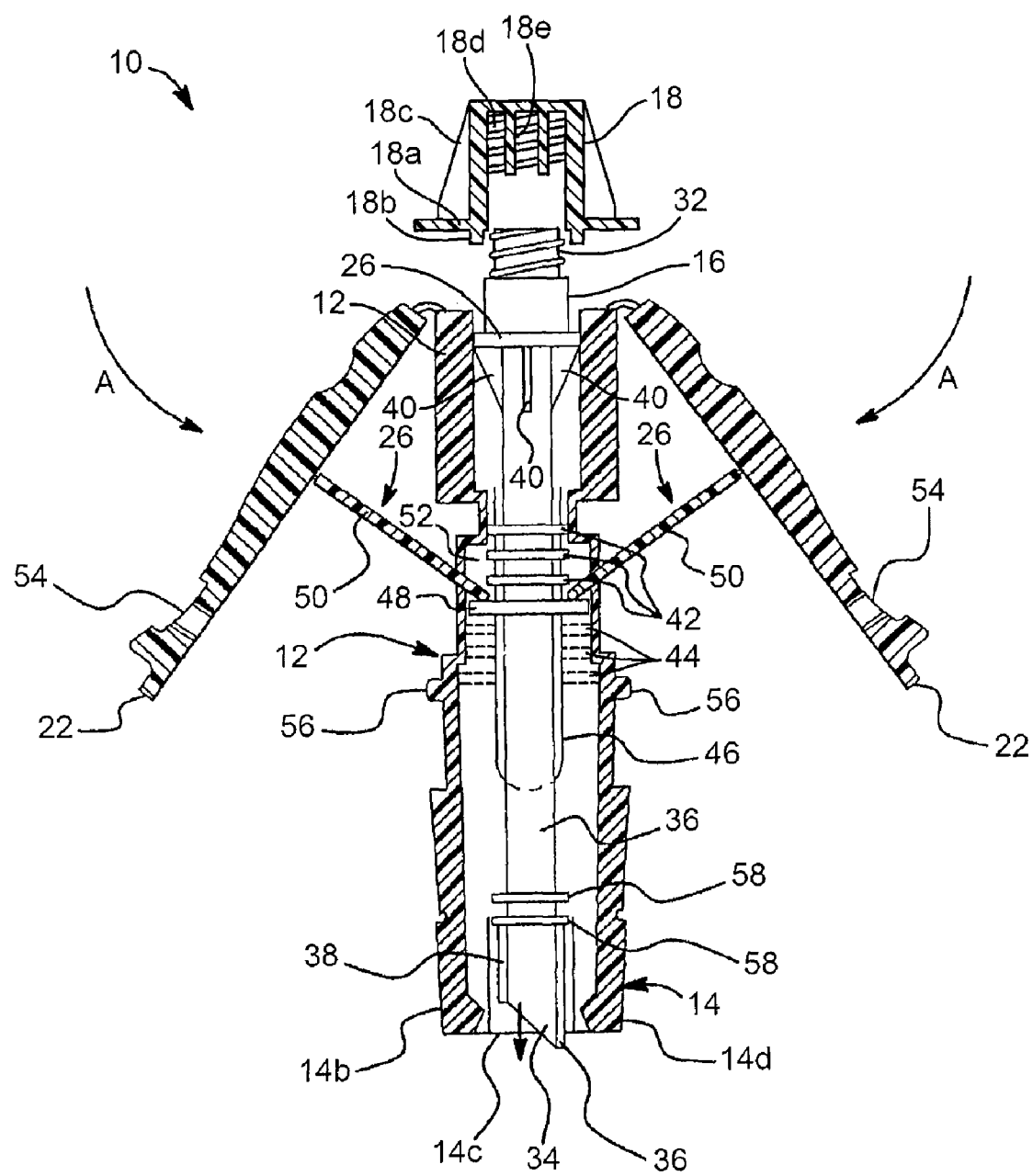
FIG. 4 is a side sectioned view of the access port of FIGS. 1-3 in a non-perforating position.
Figure 5:
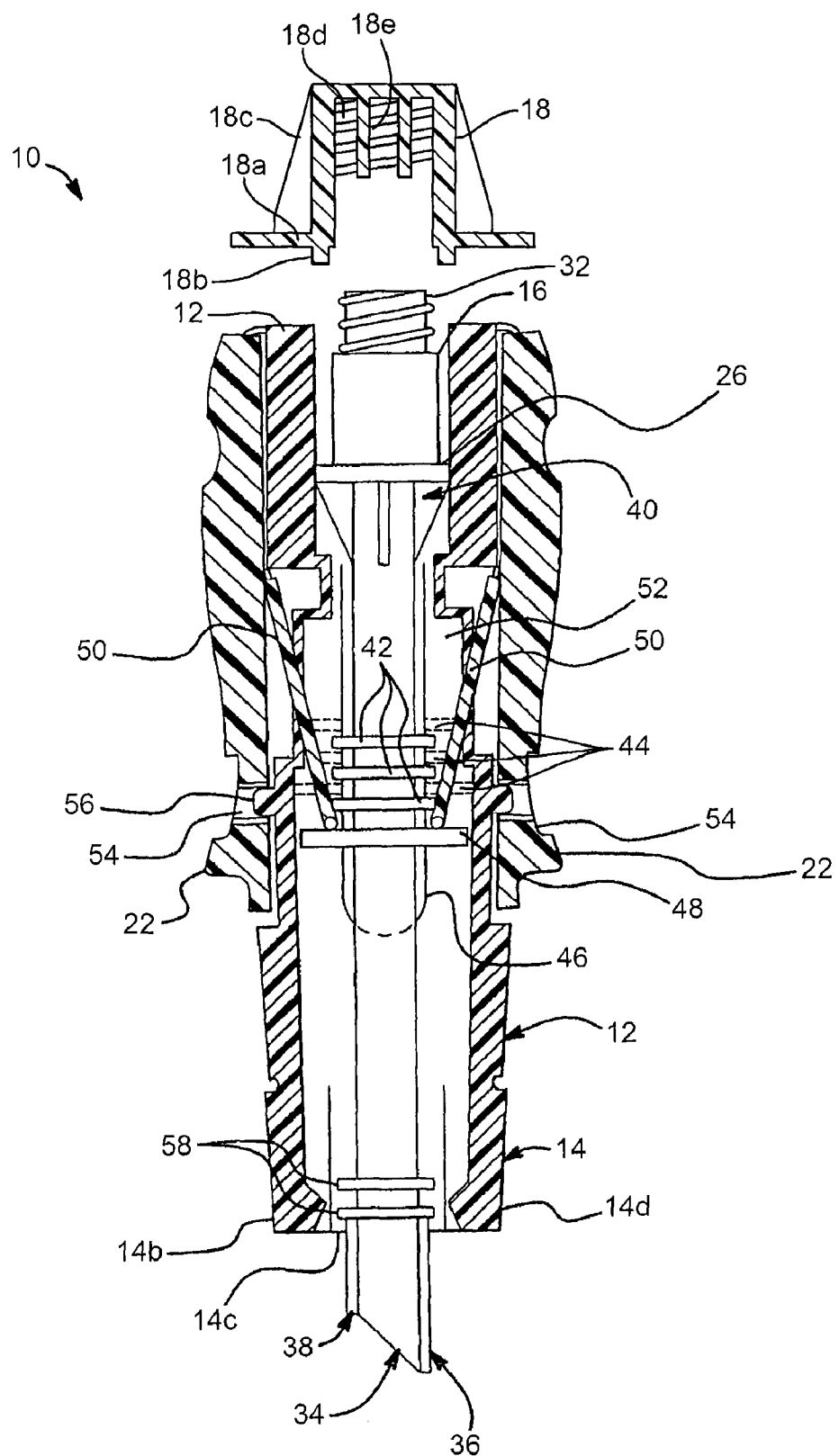
FIG. 5 is a side-sectioned view of the access port of FIGS. 1-3 in a perforating position.

As seen in FIGS. 4 and 5, perforator 16 includes a threaded end 32 that extends out the top of the shell 12. Threaded end 32 is configured to connect fluidly to a luer or other type of connector, which in turn connects to a tube or hose of an administration set. The threads of threaded end 32 also couple to a female threaded cap 18 (FIGS. 1-3), which protects threaded end 32 prior to use of perforation assembly 10.

At its opposite end, perforator 16 includes a beveled tip 34. The angle of bevel may be any suitable angle, such as thirty to sixty degrees relative to a longitudinal axis of a stem 36 of perforator 16. Beveled tip 34 in one embodiment includes ribs 38, which extend longitudinally with tip 34 and provide, when engaged into slots designed inside the valve 30, means to block the rotation of the perforator 16 when cap 18 or a luer connector of the administration set are screwed on and off.

A series of flanges extend radially outwardly from stem 36 of perforator 16. Beginning from the top, a circular flange 26 extends outwardly from a top portion of stem 36 of perforator 16. For rigidity, a plurality of gussets 40 support flange 26. Gussets 40 operate to stabilize flange 26 plunging the perforator 16.

A series of guiding flanges 42 are provided on stem 36 below flange 26. Guiding flanges 42 are designed to ease the assembly procedure of both members 50 through the aperture 52 when the perforator 16 is inserted inside the shell 12. Although not specifically illustrated, projections 44 extending inwardly from the inside wall of shell 12 are provided (FIG. 5). These projections 44 are tapered or rounded along their upper periphery to enable a ramped engagement with drive flange 48 when perforator 16 is being moved towards a bag piercing position. Projections 44 are substantially perpendicular to the wall of shell 12 along their lower periphery to provide a locking engagement with drive flange 48 when perforator 16 has been moved or snapped to its bag piercing position.

As seen in FIGS. 1-5, shell 12 includes a plurality of U-shaped cutout flaps 46. Cutout flaps 46 can flex slightly relative to the remainder of shell 12. Projections 44 are located on the inner surface of flaps 46. As perforator 16 is moved relative to shell 12, flaps 46 flex slightly outwardly to enable drive flange 48 to move past projections 44 and eventually snap-fit between and/or around projections 44. The engagement between drive flange 48 and projections 44 precludes the removal of perforator 16 from container 100 after the container is pierced: This engagement may also provide tactile and/or audible feedback to the user indicating that container 100 is being pierced.

Figure 2:
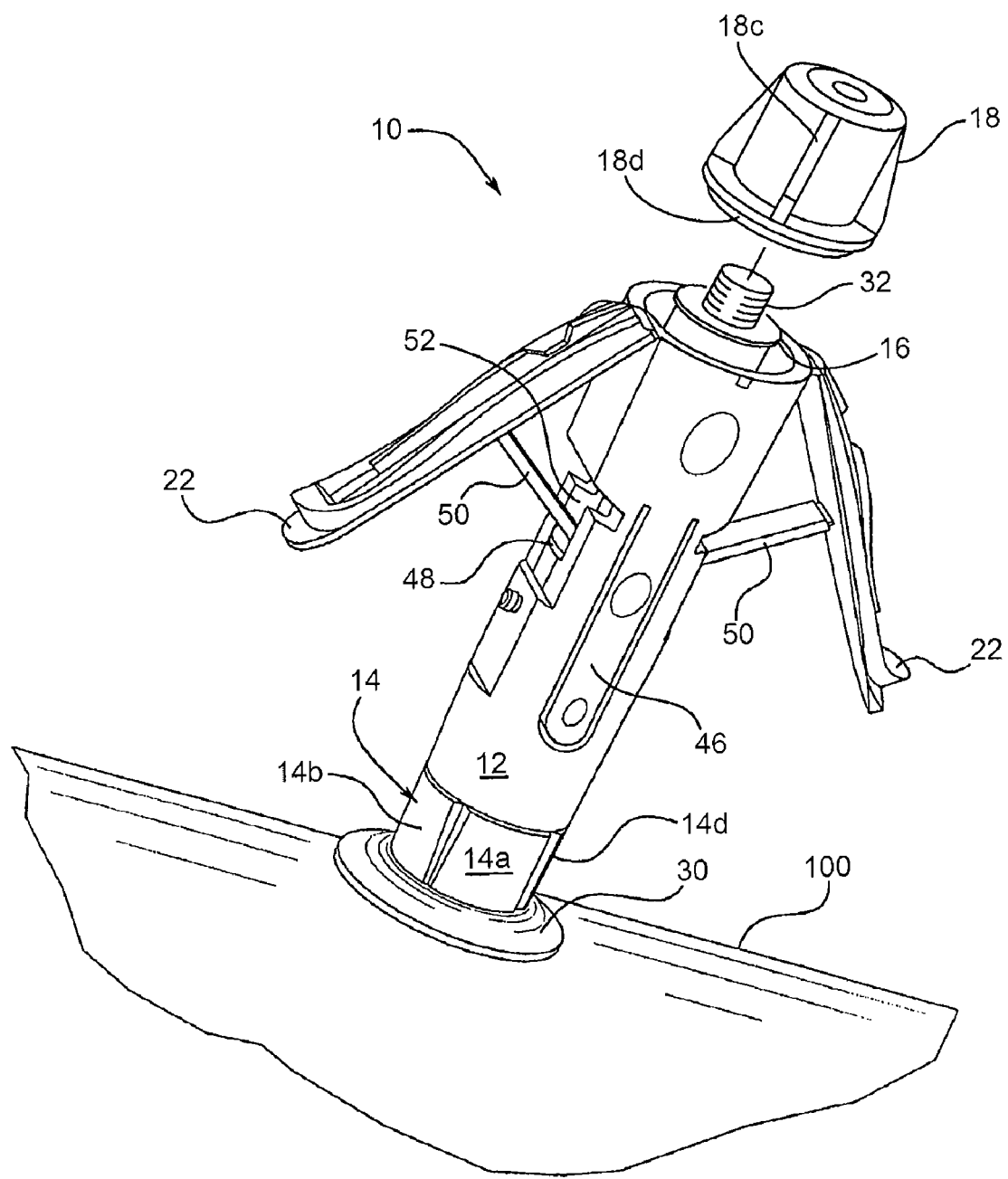
FIG. 2 is another perspective view of the fluid container, valve and access port of FIG. 1.
Figure 3:
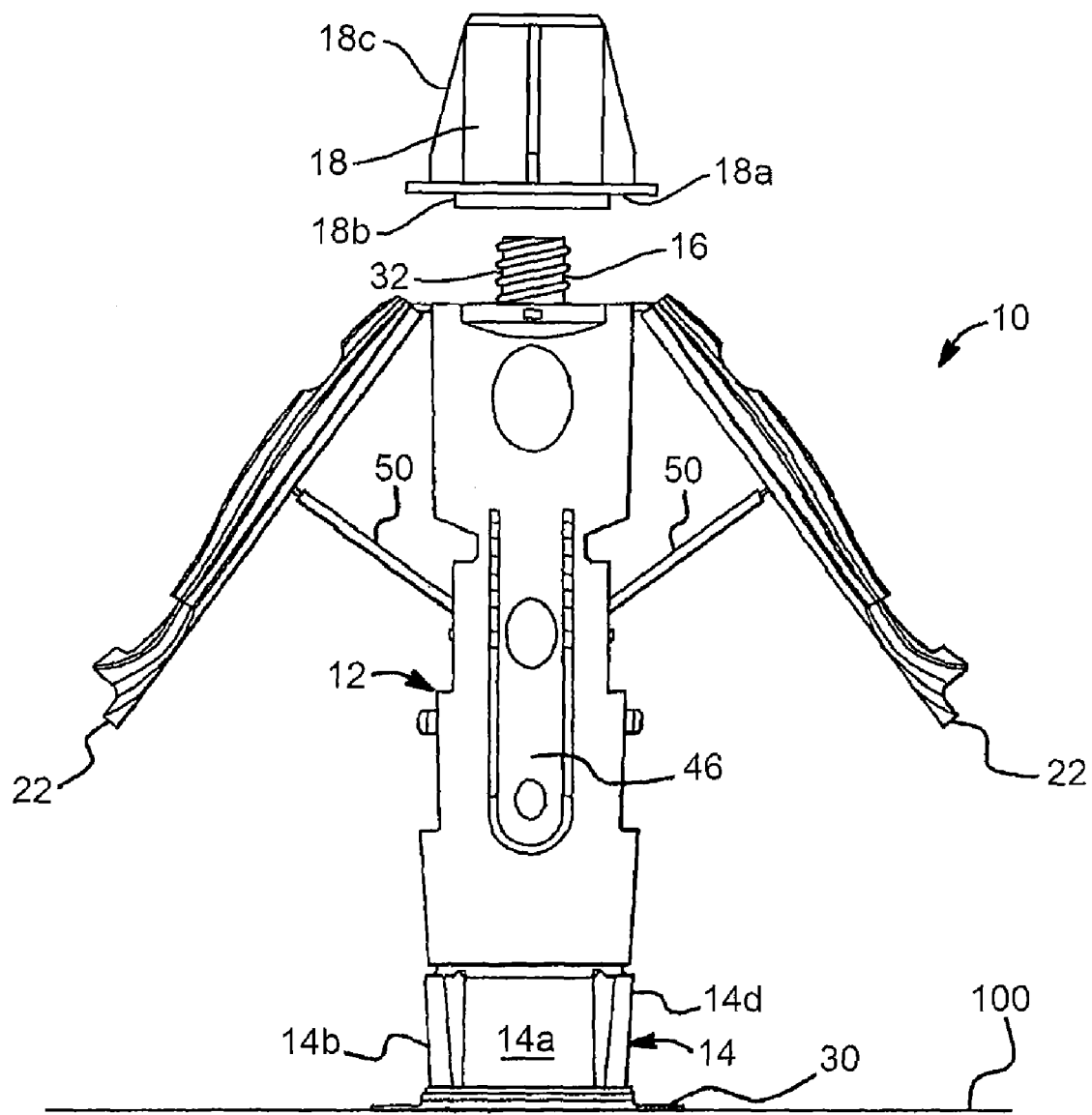
FIG. 3 is a side elevation view of the access port of FIGS. 1-2.

As seen in FIGS. 2, 4, and 5, a drive flange 48 is provided on stem 36 below guiding flanges 42. Members 50 are coupled hingedly at first ends to arms 22 of shell 12. Members 50 extend through apertures 52 defined by shell 12 and contact the top surface of drive flange 48 at their second ends. Arms 22 in turn are coupled hingedly to the top of the body of shell 12.

FIGS. 4 and 5 illustrate the piercing motion of perforation assembly 10. Once integrated cap 18 is removed, manual pressure is applied to the outside of arms 22. As illustrated by the arrows A of FIG. 4, the manual pressure causes arms 22 to rotate towards the body of shell 12. The rotation of arms 22 causes each member 50 to rotate towards its respective arm 22. The rotation of members 50 causes drive flange 48 and perforator 16 to move downwards (towards container 100).

As seen in FIGS. 4 and 5, when perforator 16 is in the piercing position, arms 22 and members 50 are collapsed onto shell 12 and in substantial alignment with the body of shell 12. Perforator 16 is moved fully downwards. Flange 48 is locked between/about projections 44. Also, arms 22 define at their distal ends locking openings 54 that engage and snap-fit onto knobs 56 extending from shell 12. The friction or snap-fit engagement of openings 54 and knobs 56: (i) serves further to hold perforation assembly 10 in a locked position once piercing engagement and fluid connection is made with container 100, (ii) provide tactile and/or audible feedback to the user indicating that container 100 is being pierced and (iii) preclude the removal of perforator 16 from container 100 after the container is pierced.

A pair of sealing flanges 58 extends from stem 36, near beveled tip 34 and ribs 38. Sealing flanges 58 define a groove in which an appropriate sealing gasket sits (not represented). The gasket seal helps create a liquid-tight and bacteria-tight seal between the perforator 16 and the valve 30. This seal also helps ensure sterile delivery of the contents of the container 100 through the perforation assembly 10.

As seen in FIGS. 1-4, perforator 16 is attached initially to a removable integrated safety cap 18. When the cap is threaded onto perforator 16, the cap restrains axial movement within shell 12 to puncture the film, even if inward force is applied to arms 22. Lip 18a and downward extending ring protrusion 18b of cap 18 also preferably fit closely against shell 12.

The cap preferably also includes a plurality of exterior ribs or gripping flanges 18c. Ribs 18c add stability to the cap. These features make it easier for a user to grasp and remove the cap. Cap 18 also preferably connects to the non-penetrating end of the penetrator with internal female threads 18d, mating to threads 32 on the penetrator. In a preferred embodiment threads 32 and 18d may be the threads of female and male luer lock connectors.

As can be better seen in FIG. 4, ring protrusion 18b fits between shell 12 and perforator 16. The width of design of the ring protrusion may be selected to fit tightly against the shell, the perforator, or both. At least one of these fits is tight enough so that it causes friction or a slight interference when the cap is placed on the access port or when the cap is removed from the access port. In one embodiment, there is a tighter fit between the ring protrusion 18a of the cap and the upper portion of the perforator 16 than between the ring protrusion 18a and the upper portion of shell 12. This helps to prevent movement of the perforator and helps to ensure the sterility of the connector at the upper end of the perforator. This friction or tight fit also prevents rotation of the shell around the perforator as long as the cap remains in place on the access port. The interference between the perforator and the cap ring is preferably higher than the interference between the cap ring and the shell.

The operator connects a device such as an administration set with luer connector to the perforator 16 in a fluid-tight manner by removing cap 18 and connecting the device via threads 32 located at the top of the perforator 16. With the perforation assembly 10 installed in the valve 30 and the safety cap 18 removed, arms 22 can be then pressed inwardly to cause perforator 16 to move and puncture the solution container 100. Fluid flows from container 100, through stem 36 of perforator 16, through the administration set, and to a patient or other container. In one embodiment, different fluids within container 100 are premixed before the above fluid connection is made.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

What is claimed is:

1. An access port comprising:
  a shell adapted for connection to a fluid container;
  a perforator located within the shell and capable of axial movement therein, the perforator including a first end configured to pierce a medical fluid container and a second end configured to connect to a fluid carrying device;
  a removable safety cap configured to fit over the second end, the cap adapted to impede axial movement of the perforator while coupled to the second end; and
  at least one arm connected pivotally to the shell and mechanically coupled to the perforator, whereby pivoting the arm moves the perforator axially with respect to the shell.

2. The access port of claim 1, wherein the safety cap further comprises a ring protrusion configured to fit inside the shell to seal the shell, and wherein the ring protrusion is in frictional engagement with the perforator or the shell.

3. The access port of claim 2, wherein the ring protrusion and an upper portion of the perforator are configured to fit tightly together.

4. The access port of claim 2, wherein the ring protrusion is in frictional engagement with both the shell and the perforator.

5. The access port of claim 2, wherein an inner surface of the ring protrusion extending is configured to provide an interference fit with an outer surface of the perforator.

6. The access port of claim 1, wherein the shell comprises a distal end and the safety cap further comprises a lip that abuts the distal end of the shell.

7. The access port of claim 1, further comprising a member coupled to the arm, the member extending through an aperture defined by the shell and contacting the perforator.

8. The access port of claim 1, further comprising a plurality of ribs on an outer surface of the safety cap.

9. The access port of claim 1, further comprising a medical fluid container made from a flexible film, the container coupled to the access port.

10. An access port comprising:

a perforator including a piercing end configured to pierce a medical fluid container and a connecting end adapted to connect to a fluid conduit;

a shell positioned outside of the perforator, the shell including a body and a pair of arms connected hingedly to the body and extending angularly away from the body toward the piercing end of the perforator, the shell further including members each having a first end connected hingedly to one of the arms and a second end contacting the perforator, the members operable to push the perforator towards the medical fluid container when the arms are pushed towards the body of the shell; and a cap configured to cover the connecting end of the perforator, the cap configured to prevent the perforator from piercing the medical fluid container until the cap is removed.

11. The access port of claim 10, wherein the cap further comprises a ring protrusion fitting within the shell with a friction fit, wherein the friction fit results from a close fit of the ring protrusion with at least one of an inner diameter of the shell and an outer diameter of the perforator.

12. The access port of claim 10, wherein the first end of each of the members is hingedly connected to a middle part of one of the arms.

13. The access port of claim 10, wherein the perforator comprises at least one outwardly extending flange and the second end of each of the members contacts the perforator at the flange.

14. The access port of claim 10, wherein the perforator and the shell are configured to provide audible or tactile feedback when the perforator is moved with respect to the shell.

15. The access port of claim 10, wherein the shell is configured to provide audible or tactile feedback when the arms are fully moved towards the body of the shell.

16. The access port of claim 10, wherein the perforator and the shell are configured to establish locking engagement therebetween after the perforator has been moved to a piercing position with respect to the shell.

17. A medical fluid container assembly comprising:
at least one flexible film forming a fluid tight container;
an access port with a shell configured to be coupled to the container; and
a perforator located within the shell and capable of axial movement therein, the perforator including a first end configured to pierce a medical fluid container and a second end configured to connect to a fluid carrying device;
a removable safety cap coupled to the second end, the cap adapted to impede axial movement of the perforator while coupled to the second end; and
at least one arm connected pivotally to the shell and mechanically coupled to the perforator, whereby pivoting the arm moves the perforator axially with respect to the shell.

18. The assembly of claim 17, wherein the safety cap fits frictionally against both the shell and the perforator.

19. The assembly of claim 17 further comprising a medical fluid for parenteral administration disposed within the container.

20. An access port comprising:
a perforator including a piercing end configured to pierce a medical fluid container and a connecting end adapted to connect to a fluid conduit;
a shell positioned outside of the perforator, the shell including a body and a pair of arms connected hingedly to the body and extending angularly away from the body toward the piercing end of the perforator, the shell further including members each having a first end connected hingedly to one of the arms and a second end contacting the perforator, the members operable to push the perforator towards the medical fluid container when the arms are pushed towards the body of the shell, wherein the arms are configured to lockingly engage with the body of the shell when the arms are fully moved towards the body of the shell; and
a cap configured to cover the connecting end of the perforator, the cap configured to prevent the perforator from piercing the medical fluid container until the cap is removed.

* * * * *